United States Patent [19]

Matsuzawa et al.

[11] 4,011,272
[45] Mar. 8, 1977

[54] PROCESS FOR PRODUCING TERTIARY BUTYL ALCOHOL

[75] Inventors: Hideo Matsuzawa; Minoru Ikeda; Yukinobu Sugimoto; Shuji Uchida, all of Ohtake, Japan

[73] Assignee: Mitsubishi Rayon Co., Ltd., Tokyo, Japan

[22] Filed: July 9, 1975

[21] Appl. No.: 594,354

Related U.S. Application Data

[63] Continuation-in-part of Ser. No. 479,037, June 13, 1974, abandoned.

[30] Foreign Application Priority Data

July 25, 1973 Japan .......................... 48-83719
Mar. 7, 1974 Japan .......................... 49-26491

[52] U.S. Cl. .................... 260/641; 260/475 N; 260/476 R; 260/485 R; 260/486 R; 260/487; 260/497 R; 260/638 R; 260/682
[51] Int. Cl.² .................................. C07C 29/04
[58] Field of Search ............................. 260/641

[56] References Cited
UNITED STATES PATENTS

| | | | |
|---|---|---|---|
| 2,477,380 | 7/1949 | Kreps et al. | 260/641 |
| 2,830,091 | 4/1958 | Friedman et al. | 260/641 |
| 3,088,969 | 5/1963 | Callahan et al. | 260/641 |
| 3,257,469 | 6/1966 | Kovach | 260/641 |
| 3,328,471 | 6/1967 | Kronig et al. | 260/641 |
| 3,397,250 | 8/1968 | Nambu | 260/641 |
| 3,810,849 | 5/1974 | Massie | 260/641 |
| 3,862,236 | 1/1975 | Scharff et al. | 260/638 R |
| 3,932,306 | 1/1976 | Rona | 260/641 |

*Primary Examiner*—Joseph E. Evans
*Attorney, Agent, or Firm*—Oblon, Fisher, Spivak, McClelland & Maier

[57] ABSTRACT t-Butyl alcohol is produced by reacting isobutylene with an aqueous organic acid solution in the presence of an acidic ion-exchanger. t-Butyl alcohol can be produced by this process from a mixed gas containing isobutylene and n-butene. The process is also applicable for separation of isobutylene from a mixed gas containing isobutylene and n-butene.

5 Claims, 2 Drawing Figures

PROCESS FOR PRODUCING TERTIARY BUTYL ALCOHOL

CROSS REFERENCE TO RELATED APPLICATION

This application is a continuation-in-part of application Ser. No. 479,037, filed June 13, 1974, now abandoned.

This invention relates to a process for producing t-butyl alcohol from isobutylene. More particularly, this invention relates to a process for producing t-butyl alcohol by allowing isobutylene to react with water in the presence of an acidic ion-exchange resin and an organic acid.

Tertiary butyl alcohol has widely been used in various uses such as additives to gasoline, solvents for paints or starting materials for various compounds. For production of t-butyl alcohol from isobutylene, there has heretofore been known a process wherein an aqueous sulfuric acid solution with a concentration of 50 to 65% is used. This process comprises contacting a hydrocarbon mixture containing isobutylene with an aqueous sulfuric acid solution to convert isobutylene into t-butyl alcohol and then purifying said alcohol by separation from other mixed hydrocarbons. If necessary, said alcohol is decomposed again to produce isobutylene; thus, the process may also be applicable for purification of isobutylene. Because an aqueous solution containing 50 to 60% sulfuric acid is used in this process, materials for equipment are limited to specific kinds and equipment life is short. In addition, the process is accompanied with side reactions such as dimerization and trimerization of isobutylene and also with high consumption of sulfuric acid.

On the other hand, there has been known a process for production of alcohols by direct hydration of olefins. For example, as is well known, butenes are directly hydrated to produce the corresponding alcohols by using phosphoric acid catalyst and tungsten oxide catalyst in an analogous manner to the process for synthesis of ethanol from ethylene. However, this process is disadvantageous in that the reaction is in equilibrium shifted toward the side of the original system at a temperature of 200° to 250° C at which the catalyst is effectively active. Therefore, the process has drawbacks in that it is required to carry out the reaction under high pressure to use water in greater excess relative to olefin, and that conversion is low.

Another known process of producing t-butyl alcohol is the direct hydration of olefins in the presence of a medium of a solid acid catalyst with a solvent which is not the same as the product being formed in the reaction as disclosed by Henke et al., U.S. Pat. No. 3,285,977. In this method, the olefin is hydrated at a temperature of 80° to 316° C under conditions which result in a reaction effluent wherein separation of an organic phase containing mainly olefins from an aqueous phase containing mainly water occurs. When the reaction is conducted over an acidic ion-exchange resin as the solid acid catalyst, the service life of the catalyst is diminished because of the high reaction temperatures. Because of the high temperatures, high conversions to produce can only be expected to be obtained with extremely large volumes of water.

A need therefore, continues to exist for a method of converting isobutylene to t-butyl alcohol at low temperatures over an ion-exchange resin catalyst.

According to the present invention, there is provided a process for producing t-butyl alcohol, comprising allowing isobutylene or a hydrocarbon mixture containing isobutylene to react with water at 20° to 120° C in the presence of an acidic ion-exchange resin and an organic acid.

According to a preferred embodiment wherein the process of the present invention is practiced in effect, t-butyl alcohol is produced by the procedure consisting of the steps of:

1. allowing isobutylene or a hydrocarbon mixture containing isobutylene to react with an aqueous organic acid solution in the presence of an acidic ion-exchanger,
2. removing unaltered hydrocarbons from the reaction mixture by distillation,
3. separating the residual reaction mixture by distillation into a mixture (A), consisting mainly of t-butyl alcohol and organic acid ester thereof, and an aqueous organic acid solution,
4. hydrolyzing said organic acid ester produced in the step (3) by treatment of the mixture (A) with acidic ion-exchanger after, if necessary, addition of water,
5. then separating the hydrolyzed product into an aqueous t-butyl alcohol solution and an aqueous organic acid solution, and
6. recycling said aqueous organic acid solution produced in the step (5) for re-use to the step (1).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

The present invention will now be described in detail in terms of an embodiment wherein acetic acid is used as the organic acid. In the initial stage of the reaction of the present invention, isobutylene is dissolved only to a slight extent in the aqueous acetic acid solution (aqueous phase), and very little of the aqueous acetic acid solution is dissolved in the isobutylene phase. As the synthesis of t-butyl alcohol gradually proceeds, the mutual solubility of the two phases is proportionally heightened and is eventually brought to the stage wherein the whole system is converted into a homogeneous phase. This is a peculiar phenomenon which relates to an attribute of t-butyl alcohol such that, in the case of the present invention, the alcohol is dissolved in substantially equal proportions in the aqueous phase and in the olefin phase. Because the present system is such that a homogeneous phase forms, the hydration reaction proceeds at a decidedly higher velocity as opposed to the present system in which a heterogeneous phase exists.

Figure 1:
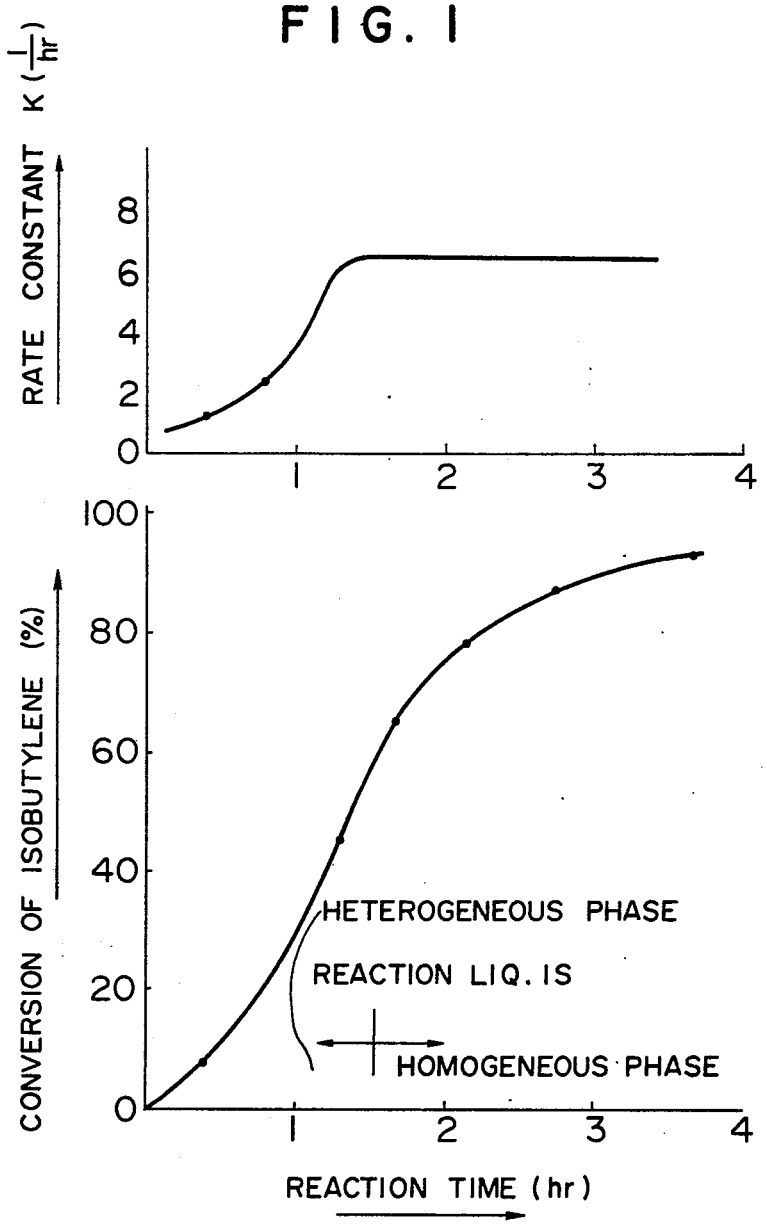
FIG. 1 is two graphs showing the reaction rate constant for the conversion of isobutylene to t-butyl alcohol as a function of time and the conversion of isobutylene as a function of time.

For example, a reaction vessel is charged with 100 moles of a mixture of n-butene containing 45 mol % of isobutylene and 140 moles each of acetic acid and water and then is maintained at a temperature of 60° C. The charge is circulated by a pump and is brought into contact with an acidic ion-exchange resin. The relation between the isobutylene conversion and the reaction time obtained in this reaction is shown in FIG. 1. From this graph, it can readily be determined that the reaction velocity remains low initially wherein the concentration of isobutylene is high, and then reaches a peak at the point at which the reaction solution becomes homogeneous because of the formation t-butyl alcohol and levels off thereafter. This fact shows that the reaction proceeds more smoothly in the homogeneous phase and, because it is homogeneous, it circumvents an otherwise possible disadvantageous impediment to the reaction which is the desorption of the reaction product from the surface of catalyst.

In FIG. 1, the reaction rate constant K represents the degree of progress of reaction excluding the possible effect thereon of isobutylene concentration, as defined by the following expression:

Rate constant K =

$$\frac{\text{Amount of isobutylene converted per unit time/Amount of catalyst}}{(\text{Isobutylene concentration})^{**} - (\text{Isobutylene concentration at equilibrium})^{*}}$$

*Concentration of isobutylene when the reaction has reached its equilibrium.
**Average concentration of the two phases in the heterogenous phase.

In view of the foregoing, it is evident that in the present invention, the reaction proceeds continously and the reaction system can be maintained in one homogenous phase at all times. For this purpose, it is desirable to conduct the reaction in a reaction vessel of the perfect-mixing type. Preferably, the reaction should be conducted therein so that the conversion of isobutylene increases to the extent more than sufficient for the reaction product to be obtained in the form of a homogeneous phase and, where necessary, the reaction system can be subsequently transferred into some other reaction vessel to further increase the isobutylene conversion.

The hydrocarbon mixtures containing isobutylene to be used as the starting materials in the process of the present invention are not specifically limited. The hydrocarbon mixture is reacted with water at 20° to 80° C in the presence of an acidic ion exchanger and an organic acid under conditions such that the liquid product obtained is a homogeneous solution. Ordinarily, however, those consisting mainly of hydrocarbons with carbon atoms of 4 are used. A small quantity of hydrocarbons with carbon atoms of 3 or 5 may also be contained in the hydrocarbon mixtures.

According to the process of the present invention, t-butyl alcohol is cotinuously produced by reacting isobutylene with water at 20° to 80° C in the presence of an acidic ion-exchanger and a saturated aliphatic acid of 1 to 6 carbon atoms, such as acetic acid, under conditions which permit the t-butyl alcohol-water-isobutylene-carboxylic acid solution product of the reaction to occur in the form of a homogeneous solution. In the process, the conversion of isobutylene to product is enhanced by homogenizing the reaction solution in a complete-mixing type reaction vessel. Thereafter, if necessary, the conversion of isobutylene can still be further enhanced in a desired reaction vessel. The reaction results in the conversion of a great part of the isobutylene to t-butyl alcohol, wherein a portion of the alcohol is obtained as the t-butyl ester of the organic acid used. The aqueous organic acid solution containing said alcohol is distilled to obtain t-butyl alcohol. The residual aqueous organic acid solution may be used again for reaction with isobutylene.

In the process of the present invention, there hardly occurs dimerization, trimerization or other polymerization of isobutylene. The reaction proceeds selectively between isobutylene and water, and other reactions such as conversion of n-butenes contained in the starting hydrocarbon to sec-butyl alcohol or conversion of organic acids to sec-butyl esters are almost negligible. Accordingly, purification of the reaction can be very simple.

Various organic acids may be used in the present invention. For example, there may be used saturated aliphatic carboxylic acids with carbon atoms of 1 to 6 such as formic acid, acetic acid, propionic acid, butyric acid, oxalic acid or adipic acid; aromatic carboxylic acids with carbon atoms of 7 to 8 such as benzoic acid or terephthalic acid; and halogen-substituted acetic acids such as chloroacetic acid, dichloroacetic acid or trichloroacetic acid. Alternatively, polymerizable organic acids such as acrylic acid or methacrylic acid may also be used; polymerization inhibitors are required to be added when these polymerizable acids are employed. Among the organic acids as mentioned above, those having high solubility in water are preferred. From this standpoint, saturated aliphatic acids with carbon atoms of 1 to 6 are preferred as the organic acids. In particular, in view of the price and stability, acetic acid is the most preferable substance. The concentration of the aqueous organic acid solution is not specifically limited. As the concentration of the organic acid is higher, the rate of formation of t-butyl alcohol is accelerated, but the content of t-butyl ester of the organic acid in the reaction product is increased. This, however, is not regarded as a vital drawback because the t-butyl ester formed can easily be hydrolyzed to an organic acid and t-butyl alcohol. Namely, after the t-butyl ester and t-butyl alcohol are separated from the reaction product, it is admixed with water, if necessary, and then contacted with a strongly acidic ion-exchange resin to hydrolyze the ester. For example, during purification of t-butyl alcohol by distillation, a portion of liquid is extracted at an intermediate position of destillation tower, contacted with an acidic ion-exchange resin to hydrolyze the t-butyl ester, and then recycling the hydrolysate to the distillation tower. The reaction may thereby be conducted without lowering the coefficient of utilization of isobutylene. Accordingly, the concentration of an organic acid employed may be determined most suitably from an economical standpoint. In general, the organic acid is used in an amount to give a proportion of 30 to 500 moles per 100 moles of water, and the water may be used in an amount to give a proportion of 100 to 400 moles per 100 moles of isobutylene.

The reaction temperature is from 20° to 80° C. As the reaction temperature is lowered, the reaction is advantageous in equilibrium relation but the rate of reaction is retarded. On the contrary, if the reaction temperature is too high, not only the reaction is disadvantageous in equilibrium relation but also the catalyst life is shortened. Accordingly, the reaction temperature preferably falls within the range of 25° to 70° C. The reaction pressure may range from about atmospheric up to 11 atmospheres. Usually, it is preferably increased to the extent to liquefy hydrocarbon mixtures. The reaction time, which should be determined suitably according to the amount of the catalyst, the temperature, the organic acid employed and the concentration thereof, is ordinarily from 30 minutes to 10 hours. The reactor system may either be batchwise or continuous, the latter being usually performed. Ion-exchangers used as the catalyst are not specifically limited but any strong acidic ion-exchanger may be used. Above all, a porous ion-exchanger is preferably used.

The process of the present invention may also be applicable for separation of isobutylene from a mixture of hydrocarbons having 4 carbon atoms. That is, an aqueous organic acid solution is allowed to react with a mixture of hydrocarbons containing isobutylene to convert isobutylene into t-butyl alcohol. The aqueous organic acid solution containing said alcohol is separated by distillation from the hydrocarbon mixture from which isobutylene is removed. After separation of t-butyl alcohol by distillation from the aqueous organic acid solution containing said alcohol, t-butyl alcohol can be dehydrated by a known method to obtain isobutylene. The isobutylene obtained by this process if very high in purity.

Figure 2:
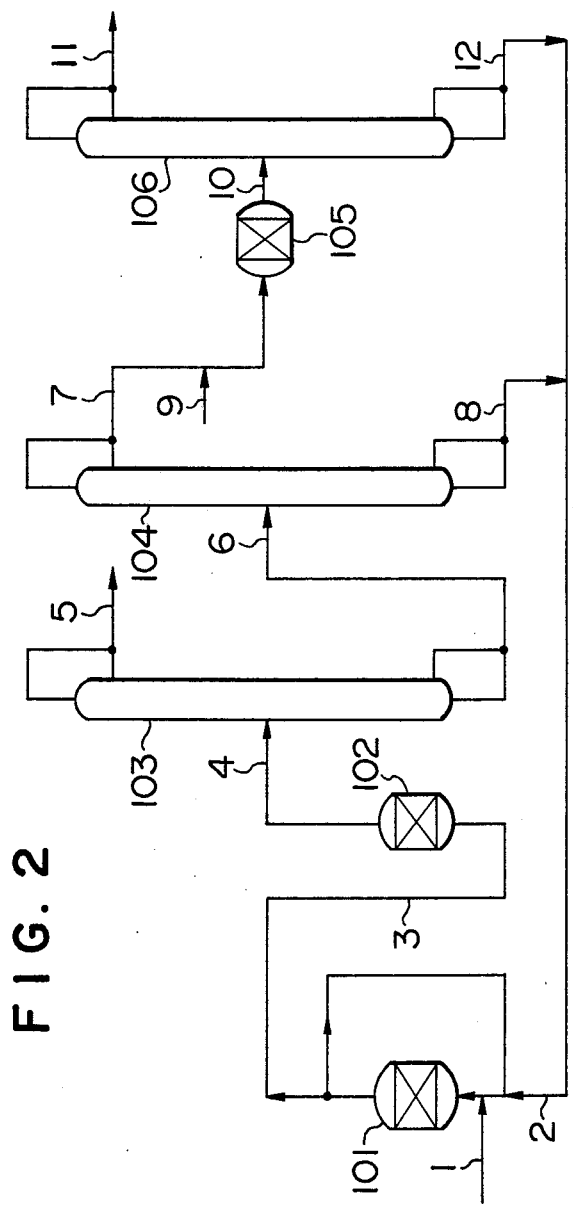
FIG. 2 is a schematic diagram of a preferred embodiment of the process of the present invention.

Referring now to the accompanying FIG. 2, wherein a flow sheet of the above preferred embodiment is shown to illustrate the process of the present invention, 101 and 102 are the first and the second reactors packed with acidic ion-exchangers, respectively. The first reactor is of a complete mixing type and the second of a plug flow type.

A complete mixing type reaction can be one which is packed with an ion-exchanger into which reactants to be charged are forced by a pump, for example. Alternatively, the reactor may be equipped with an agitator to uniformly suspend the ion-exchanger therein or fix the exchanger so that it sufficiently contacts the reactants. Any apparatus may be used, as long as the desired reaction can be uniformly conducted therein. Hydrocarbon mixture containing isobutylene is fed through line 1 and aqueous organic acid through line 2. Operation is carried out preferably under the conditions such that the fluid (in line 3) discharged out of the first reactor may be in a homogeneous phase. The fluid discharged out of the second reactor is charged through line 4 into the distillation tower for separation of hydrocarbons 103 and unaltered hydrocarbon mixture containing isobutylene is taken out therefrom through line 5. 104 shows the distillation tower for removal of organic acid. Aqueous organic acid solution is separated and taken out from the tower through line 9 to be provided for re-use. The aqueous solution containing t-butyl alcohol and t-butyl alcohol ester of organic acid taken out through line 7 is admixed, if necessary, with water supplied through line 9 and charged into the third reactor 105 packed with acidic ion-exchangers, wherein said ester is hydrolyzed. The reaction mixture is transferred through line 10 to the distillation tower 106 for separation of t-butanol and aqueous t-butanol solution is obtained through line 11. The organic acid formed by hydrolysis of said ester is taken out together with water and recycled for re-use in the first step reaction. The aqueous t-butanol solution obtained through line 11 may directly be used as starting materials for production of methacrolein or water may be removed therefrom, if necessary, according to conventional manner.

Since a strong acidic ion-exchanger can be present only when isobutylene reacts with water and absent at the time of recovery and purification of t-butyl alcohol formed in the process of the present invention, recovery and purification operations can be advantageously stable as compared with the process wherein a homogeneous system catalyst such as mineral acid is used.

Having generally described this invention, a further understanding can be obtained by reference to certain specific examples which are provided herein for purposes of illustration only and are not intended to be limiting unless otherwise specified.

EXAMPLE 1

Isobutylene is blown into a reaction vessel wherein 1.2 g equivalent of a sulfonic acid type ion-exchanger resin is suspended in a mixture of 100 moles of water and 30 moles of acetic acid. The reaction is conducted under normal pressure at 40° C. After one hour, 0.27 mole of t-butyl alcohol is formed and, after 4 hours, 0.68 mole of t-butyl alcohol. After the reaction of 4 hours, only traces of t-butyl acetate and dimer of isobutylene are to be found.

EXAMPLE 2

Isobutylene is blown into a reaction vessel wherein 5.6 gram equivalents of a sulfonic acid type ion-exchange resin are suspended in a mixture of 100 moles of water and 270 moles of acetic acid. The reaction is conducted under normal pressure at 40° C. After the reaction is continued for 2 hours, 8.25 moles of t-butyl alcohol and 1.78 moles of t-butyl acetate are formed. After 4 hours' reaction, 20.6 moles of t-butyl alcohol and 4.1 moles of t-butyl acetate are formed. Dimer of isobutylene is detected only in traces even after 4 hours' reaction.

In the following, comparative tests corresponding to Examples 1 and 2 are performed, whereby no organic acid is present.

COMPARATIVE EXAMPLE 1

Isobutylene is blown under normal pressure into a reactor equipped with a stirrer wherein 130 moles of water and 1.2 gram equivalents of a sulfonic acid type ion-exchange resin are charged. The temperature of the reaction mixture is controlled to be maintained at 40° C. The yields of t-butyl alcohol after respective reaction time are as shown below:

| Time: | 1 hour | 2 hours | 3 hours |
|---|---|---|---|
| Yield (mole): | 0.0276 | 0.0518 | 0.0735 |

No other substance such as dimer or trimer of isobutylene is detected in the reaction mixture.

COMPARATIVE EXAMPLE 2

370 moles of water, 12 moles of isobutylene and 5.6 gram equivalents of ion-exchange resin are charged into an autoclave equipped with a stirrer. The reaction is carried out while maintaining the temperatue at 60° C. The pressure during the reaction is 8 atm. After the reaction of 2 hours, the amount of t-butyl alcohol formed is 0.50 mole. No other substance such as dimer or trimer of isobutylene is found.

As illustrated by the foregong comparative example, the absence of the organic acid which results in a minimum of t-butyl alcohol, renders the reaction infeasible. It is readily apparent, on the other hand, that when the reaction is conducted in a homogeneous phase in the presence of the organic acid, t-butyl alcohol is obtained at temperatures notably lower than those employed in the prior art at a rate high enough to warrant commercial feasibility of the reaction.

EXAMPLE 3

This Example described about production of t-butyl alcohol by a pilot plant of which flow sheet is as shown in the accompanying drawing. The composition of a mixed gas of hydrocarbons used as the starting material is shown in Table 3. The starting material is fed through line 1 into the first reactor at the rate of 100 moles/hour. A fluid consisting mainly of 1:1 mole mixture of acetic acid and water is supplied through line 2, each at the rate of 140 moles/hour, into the first reactor. The first reactor is packed with 1.3 Kg of sulfonic acid type cationic ion-exchange resins. The temperature in said reactor is controlled to be maintained at 70° C. The fluid supplied through line 3 into the second reactor is in state of a homogeneous phase. The second reactor is packed with 1.1 Kg of sulfonic acid type cationic ion-exchange resins and the temperature therein is maintained at 70° C. The composition of the fluid removed from line 4 is shown in Table 4. This table shows that conversion of isobutylene is 93%, selectivity to t-butyl acetate 7%, with traces of isobutylene polymers. There can hardly be detected sec-butyl alcohol or sec-butyl acetate. The composition of the hydrocarbon mixture containing unaltered isobutylene is shown in Table 3. The composition of the tower distillate stripped of acetic acid (from line 7) is shown in Table 4. The rate of water supplied through line 9 is 60 moles/hour. The third reactor 105 is packed with 1.3 Kg of sulfonic acid type cationic ion-exchange resins and operated at 80° C. The hydrolysis degree of t-buty acetate is 95%. The composition of the aqueous t-butyl alcohol solution obtained from line 11 is shown in Table 4. Isobutylene in this composition is recovered as vent gas and can be provided for re-use.

Table 3

| Components | Line 1 | Line 5 |
|---|---|---|
| Isobutylene | 45 mole % | 5.3 mole % |
| 1-butene | 23.2 mole % | 39.9 mole % |
| 2-butene | 18.8 mole % | 32.4 mole % |
| Butane | 13.0 mole % | 22.4 mole % |

Table 4

| Components | Line 4 | Line 7 | Line 11 |
|---|---|---|---|
| Isobutylene | 1.0 mole % | — | 4.4 mole % |
| Isobutylene polymers | trace | trace | trace |
| t-butyl alcohol | 12.9 mole % | 72.7 mole % | 59.9 mole % |
| t-butyl acetate | 1.0 mole % | 5.5 mole % | 0.23 mole % |
| sec-butyl alcohol | 0 | 0 | 0 |
| sec-butyl acetate | 0 | 0 | 0 |
| Acetic acid | 48.5 mole % | 0 | 0 |
| Water | 36.6 mole % | 21.8 mole % | 35.5 mole % |

EXAMPLE 4

Isobutylene is blown into a reactor wherein 5.5 gram equivalents of sulfonic acid type ion-exchange resins are suspended in a mixture of 100 moles of water and 220 moles of propionic acid. The reactor is operated under normal pressure at the temperature of 60° C. After 2 hours of the reaction, 23.2 moles of t-butyl alcohol and 0.7 mole of t-butyl propionate are found to be formed in the reaction mixture. Dimer of isobutylene is detected only in traces.

EXAMPLE 5 t-Butyl alcohol was continuously synthesized by using a perfect-mixing type reaction system provided with a reaction vessel packed with a sulfonate type ion-exchange resin and a pump capable of circulating the reaction solution.

A hydrocarbon mixture of 4 carbon atoms containing 45 mole % of isobutylene was used as the isobutylene source. This mixture was supplied at a rate of 50 moles/hour. An equimolar solution of water and acetic acid was supplied at a rate of 80 moles/hour. The reaction vessel was maintained at a constant level of 50° C and it contained 4 liters of catalyst. The space velocity was calculated as 2 L/L. hr, and the pressure was maintained at 4.5 kg/cm$^2$G. The liquid discharged from the reaction vessel formed a homogeneous phase at this pressure. The composition of the liquid obtained is shown in the following table. Calculations show that the conversion of isobutylene reached 70%.

Table 5

|  | mole % |
|---|---|
| Isobutylene | 5.9 |
| Other hydrocarbons | 24.1 |
| t-Butyl alcohol | 12.9 |
| t-Butyl acetate | 0.88 |
| Acetic acid | 34.1 |
| Water | 22.1 |

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for continuously producing t-butyl alcohol, which comprises reacting isobutylene with water at 20° to 80° C in the presence of an acidic ion-exchanger and from 30 to 500 moles per 100 moles of water of a saturated aliphatic carboxylic acid having from 1–6 carbon atoms under conditions such that the liquid product obtained is a homogeneous solution.

2. A process according to claim 1 wherein said isobutylene is present in a mixture of hydrocarbons having 3 to 5 carbon atoms.

3. A process according to claim 1 wherein the saturated aliphatic carboxylic acid is acetic acid.

4. A continuous process for producing t-butyl alcohol by reacting isobutylene with water at 20° to 80° C in the presence of an acidic ion-exchanger and from 30 to 500 moles per 100 moles of water of a saturated aliphatic acid having 1 to 6 carbon atoms under conditions which permit the t-butyl alcohol-water-isobutylene-carboxylic acid solution product of the reaction to occur in the form of a homogeneous solution, which comprises the steps of:

1. enhancing the conversion of isobutylene by homogenizing the reaction solution;
2. removing unaltered hydrocarbons from the reaction mixture by distillation;
3. separating the residual reaction mixture by distillation into a mixture (A), consisting mainly of t-butyl alcohol and organic acid ester thereof, and an aqueous organic acid solution;
4. hydrolyzing said organic acid ester produced in the step (3) by treatment of the mixture (A) with an acidic ion-exchanger;
5. separating the hydrolyzed product into an aqueous t-butyl alcohol solution and an aqueous organic acid solution; and
6. recycling said aqueous organic acid solution produced in the step (5) for re-use to the step (1).

5. The process of claim 4, which further comprises: enhancing the conversion of isobutylene to t-butyl alcohol by passing the reaction solution from step (1) into a plug flow reaction vessel packed with an acidic ion-exchanger prior to step (2).

* * * * *